United States Patent [19]

Lang

[11] Patent Number: 5,073,574

[45] Date of Patent: Dec. 17, 1991

[54] TETRAZOLYL SUBSTITUTED BENZONITRILES AND ANTI-TUMOR USE THEREOF

[75] Inventor: Marc Lang, Rixheim, France

[73] Assignee: Ciba-Geigy Corporation, Ardsley, N.Y.

[21] Appl. No.: 550,426

[22] Filed: Jul. 10, 1990

[30] Foreign Application Priority Data

Jul. 14, 1989 [CH] Switzerland .......................... 2644/89
Jan. 30, 1990 [CH] Switzerland ............................ 283/90

[51] Int. Cl.⁵ .................... C07D 257/04; A61K 31/41
[52] U.S. Cl. ...................................... 514/381; 548/254
[58] Field of Search ........................ 548/254; 514/381

[56]  References Cited

U.S. PATENT DOCUMENTS

| | | | |
|---|---|---|---|
| 3,894,033 | 7/1975 | Holland | 548/252 |
| 4,703,053 | 10/1987 | Connor et al. | 548/254 |
| 4,749,713 | 6/1988 | Bowman et al. | 514/341 |
| 4,801,594 | 1/1989 | Hirsch et al. | 546/276 |
| 4,845,227 | 7/1989 | Hirsch et al. | 514/340 |
| 4,937,250 | 1/1990 | Bowman et al. | 514/341 |
| 4,943,574 | 7/1990 | Raeymaekers et al. | 514/383 |
| 4,978,672 | 12/1990 | Bowman et al. | 514/383 |

FOREIGN PATENT DOCUMENTS 165778 12/1985 European Pat. Off. .
236940  9/1987 European Pat. Off. .
293978 12/1988 European Pat. Off. .

*Primary Examiner*—David B. Springer
*Attorney, Agent, or Firm*—Irving M. Fishman

[57]  ABSTRACT

Compounds of formula I,

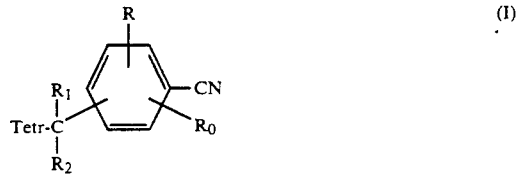

wherein Tetr, R, $R_0$, $R_1$ and $R_2$ are as defined in the description, have valuable pharmaceutical properties and are especially effective against tumors. They are prepared in a manner known per se.

14 Claims, No Drawings

TETRAZOLYL SUBSTITUTED BENZONITRILES AND ANTI-TUMOR USE THEREOF

The invention relates to compounds of formula I,

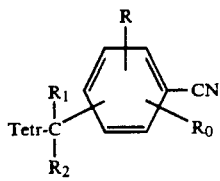

wherein Tetr is tetrazolyl; $R_1$ and $R_2$ are each independently of the other hydrogen, unsubstituted or substituted lower alkyl, lower alkenyl, aryl, hetaryl, aryl-lower alkyl, cycloalkyl, cycloalkyl-lower alkyl, lower alkylthio, arylthio or aryl-lower alkylthio; or $R_1$ and $R_2$ together are $C_4$–$C_6$ straight-chain alkylene that is unsubstituted or substituted, or are a group $-(CH_2)_m-1,2$-phenylene$-(CH_2)_n-$, wherein m and n are each independently of the other 1 or 2 and 1,2-phenylene is unsubstituted or substituted, or are lower alkylidene that is unsubstituted or mono- or di-substituted by aryl; and R and $R_0$ are each independently of the other hydrogen or lower alkyl; or R and $R_0$ together, located at adjacent carbon atoms of the benzene ring, form a benzo group that is unsubstituted or substituted; and salts thereof, to processes for the preparation of those compounds, to pharmaceutical preparations containing those compounds, and to the use of those compounds for the therapeutic treatment of the human or animal body or for the manufacture of pharmaceutical preparations.

The compounds of formula I that contain an asymmetric carbon atom can each be in the form of a racemate or in the form of an R- or S-enantiomer. The invention relates to all these forms and, for example, also to diastereoisomers and mixtures thereof which may occur when there are two or more asymmetric centres in the molecule, and also to geometric isomers, for example cis- and trans-isomers, when the molecule contains a double bond.

The general terms used hereinbefore and hereinafter preferably have the following meanings within the scope of this Application:

The prefix "lower" denotes a radical having up to and including 7, especially up to and including 4, and more especially 1 or 2, carbon atoms.

Lower alkyl is, for example, n-propyl, isopropyl, n-butyl, isobutyl, sec.-butyl, tert.-butyl, n-pentyl, neopentyl, n-hexyl or n-heptyl, preferably ethyl and especially methyl.

Lower alkoxy is, for example, methoxy or ethoxy.

Halogen is especially chlorine and bromine, but may also be fluorine or iodine.

Tetrazolyl is, for example, 1- or 2-tetrazolyl, or 1- or 2-tetrazolyl substituted in the 5-position, but may also be 5-tetrazolyl. Tetrazolyl is especially 1- or 2-tetrazolyl.

1- or 2-Tetrazolyl substituted in the 5-position can contain as substituent, for example, lower alkyl, aryl-lower alkyl or acyl, for example lower alkanoyl.

Aryl is, for example, phenyl or naphthyl, such as 1- or 2-naphthyl. The phenyl and naphthyl radicals may be unsubstituted or substituted, especially as indicated below for phenyl. Aryl is preferably phenyl that is unsubstituted or substituted by one or more, especially one or two, substituents from the group consisting of lower alkyl, lower alkoxy, hydroxy, lower alkanoyloxy, nitro, amino, halogen, trifluoromethyl, carboxy, lower alkoxycarbonyl, (amino, lower alkylamino or di-lower alkylamino)-carbonyl, cyano, lower alkanoyl, arylcarbonyl, lower alkylsulfonyl and (amino, lower alkylamino or di-lower alkylamino)-sulfonyl. Aryl is especially phenyl that is unsubstituted or substituted by lower alkyl, lower alkoxy, cyano or by halogen, and more especially is phenyl.

Aryl-lower alkyl is, for example, phenyl-lower alkyl and especially benzyl.

Hetaryl is a heterocyclic aromatic radical which is usually bonded via a carbon atom. Hetaryl is a mono-, bi- or poly-cyclic aromatic radical containing at least one ring hetero atom, preferably a ring hetero atom from the group consisting of nitrogen, oxygen and sulfur. Monocyclic heteroaromatic radicals and monocyclic heteroaromatic radicals that contain a fused-on benzo ring are preferred. Each individual heterocyclic ring is formed, for example, from 3 to 7, preferably 5 or 6, ring atoms and contains, for example, up to 4 identical or different hetero atoms.

Preferred hetaryl radicals having 5 ring atoms are monoaza-, diaza-, triaza-, tetraza-, monooxa-, monothia-, oxaza-, oxadiaza-, thiaza- and thiadiaza-cyclic radicals, for example pyrrolyl, pyrazolyl, imidazolyl, triazolyl, tetrazolyl, furanyl, thienyl, isoxazolyl, oxazolyl, oxadiazolyl, isothiazolyl, thiazolyl or thiadiazolyl.

Preferred hetaryl radicals having 6 ring atoms are monoaza-, diaza- or triaza-cyclic radicals, for example pyridyl, pyridazinyl, pyrimidinyl, pyrazinyl or triazinyl.

Preferred hetaryl radicals consisting of a heterocyclic ring and a fused-on benzo ring are indolyl, isoindolyl, benzimidazolyl, benzotriazolyl, benzofuranyl, benzothienyl, benzoxazolyl, benzothiazolyl, benzoxadiazolyl, benzothiadiazolyl, quinolyl or isoquinolyl.

Hetaryl radicals may be unsubstituted or substituted, for example as indicated above for aryl radicals. Hetaryl radicals may be in various tautomeric forms, for example depending upon the nature of the substituents.

Hetaryl is preferably a radical from the group consisting of pyridyl, thienyl, indolyl and furanyl, which radical is unsubstituted or substituted as indicated above for aryl, or is a benzotriazolyl radical of formula (1),

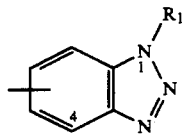

wherein $R_3$ is hydrogen or a substituent. Hetaryl is especially a radical from the group consisting of pyridyl, thienyl, indolyl and furanyl, which radical is unsubstituted or monosubstituted by lower alkyl, lower alkoxy, cyano or by halogen, or is a benzotriazolyl radical of formula (1) wherein $R_3$ is hydrogen, lower alkyl, hydroxy; unsubstituted or substituted lower alkoxy; cycloalkyl, aryl, aryl-lower alkyl, lower alkenyl or lower alkynyl. Hetaryl is especially pyridyl, thienyl, indolyl, furanyl, or benzotriazolyl that in the 1-position is unsubstituted or substituted by lower alkyl, hydroxy or by lower alkoxy, and is especially 1-lower alkyl-1H-benzotriazolyl.

Thienyl is, for example, 2- or 3-thienyl, and preferably 2-thienyl.

Pyridyl is, for example, 2-, 3- or 4-pyridyl, preferably 3- or 4-pyridyl and especially 3-pyridyl.

Furanyl is, for example, 2- or 3-furanyl, and preferably 3-furanyl.

Indolyl is, for example, 3-indolyl.

Benzotriazolyl is, for example, 4-, 5-, 6- or 7-benzotriazolyl, prererably 5-, 6- or 7-benzotriazolyl, and especially 6-benzotriazolyl.

Benzofuranyl is, for example, 4-, 5-, 6- or 7-benzofuranyl, preferably 4-benzofuranyl.

$C_4$-$C_6$ straight-chain alkylene formed by the groups $R_1$ and $R_2$ is preferably a radical —$(CH_2)_n$— wherein n is 4, 5 or 6, especially 4 or 5, for example 1,4-butylene or especially 1,5-pentylene, but may also be substituted, for example by lower alkyl.

Substituted lower alkoxy is, for example, lower alkoxy that is substituted by halogen, hydroxy, amino, lower alkylamino, di-lower alkylamino, trifluoromethyl, carboxy, lower alkoxycarbonyl, aryl, thienyl, furanyl, pyridyl, aryloxy, arylthio or by cycloalkyl. In the case of (halo, hydroxy, amino, lower alkylamino, di-lower alkylamino, aryloxy and arylthio)-lower alkoxy groups, the oxygen atom of the lower alkoxy group is preferably separated from the substituent by at least two carbon atoms.

Substituted lower alkyl is, for example, lower alkyl that is substituted by hydroxy, halogen, lower alkanoyloxy, arylcarbonyloxy, lower alkoxy, lower alkenyloxy, lower alkylthio, arylthio, lower alkylsulfonyl, carboxy, lower alkoxycarbonyl, (amino, lower alkylamino or di-lower alkylamino)-carbonyl, cyano, amino, lower alkylamino or by di-lower alkylamino.

Lower alkanoyl(oxy) is, for example, formyl(oxy), acetyl(oxy), propionyl(oxy), n-butyryl(oxy), pivaloyl(oxy) or valeroyl(oxy).

Lower alkylsulfonyl is, for example, methylsulfonyl.

When R and $R_0$ together, located at adjacent carbon atoms of the benzene ring, form a benzo group, they form a naphthalene structure together with the benzene ring.

Aryl-lower alkylthio is, for example, phenyl-lower alkylthio and especially benzylthio.

Arylthio is, for example, phenylthio.

Lower alkylthio is, for example, methylthio or ethylthio.

Lower alkenyl is, for example, vinyl, allyl, 1-propenyl, isopropenyl, 2- or 3-methallyl or 3-butenyl.

Lower alkynyl is, for example, propargyl or 2-butynyl.

Lower alkylidene is, for example, methylidene or ethylidene.

Cycloalkyl is preferably $C_3$-$C_8$- and especially $C_5$-$C_6$ cycloalkyl, which is intended to indicate that it contains 3 to 8 and 5 to 6 ring carbon atoms, respectively. It can, however, also be substituted, for example by lower alkyl.

Cycloalkyl-lower alkyl is, for example, cyclopropylmethyl, cyclopentylmethyl, cyclohexylmethyl or 2-cyclohexylethyl.

Salts of compounds according to the invention are especially pharmaceutically acceptable, non-toxic salts. For example, compounds of formula I having basic groups can form acid addition salts, for example with inorganic acids, such as hydrochloric acid, sulfuric acid or phosphoric acid, or with suitable organic carboxylic or sulfonic acids, for example acetic acid, fumaric acid or methanesulfonic acid, or with amino acids, such as arginine or lysine. Compounds of formula I having an acidic group, for example 1-tetrazolyl, form, for example, metal or ammonium salts, such as alkali metal or alkaline earth metal salts, for example sodium, potassium, magnesium or calcium salts, and ammonium salts with ammonia or suitable organic amines, such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, dibenzylamine or benzyl-$\beta$-phenethylamine. Compounds of formula I having an acidic group and a basic group can also be in the form of internal salts, that is to say in zwitterionic form.

For the purpose of isolation or purification it is also possible to use pharmaceutically unacceptable salts, for example picrates or perchlorates. Only the pharmaceutically acceptable, non-toxic salts are used therapeutically and these are therefore preferred.

The compounds of formula I according to the invention have valuable, especially pharmacologically useful, properties. In particular, they selectively inhibit the enzyme aromatase in mammals, including humans. As a result, the metabolic conversion of androgens into oestrogens is inhibited. The compounds of formula I are therefore suitable, for example, for the treatment of oestrogen-dependent diseases, including oestrogen-dependent breast cancer, especially in post-menopausal women. They are also useful, for example, in the treatment of gynaecomastia, that is to say the development of breasts in men, because the aromatisation of steroids is inhibited.

These actions can be demonstrated by in vitro tests or in vivo tests, preferably in mammals, for example guinea pigs, mice, rats, cats, dogs or apes. The dosage used is, for example, in the range of approximately from 0.001 to 10 mg/kg, preferably from 0.001 to 1 mg/kg.

The in vitro inhibition of aromatase activity can be demonstrated, for example, using the method described in J. Biol. Chem. 249, 5364 (1974). Furthermore, $IC_{50}$ values for aromatase inhibition can be obtained, for example, in vitro from enzyme-kinetic studies relating to the inhibition of the conversion of 4-$^{14}$C-androstenedione into 4-$^{14}$C-oestrone in human placental microsomes. The $IC_{50}$ values of the compounds according to the invention are about $10^{-9}$M minimum.

In vivo, the inhibition of aromatase can be demonstrated, for example, by the suppression of the ovarial oestrogen content of female rats that are injected first with mare's serum gonadotrophin and then, two days later, with human chorionic gonadotrophin, then on the following day treated p.o. with a compound of the invention and, 1 hour later, with androstenedione. A further possible method of determining aromatase inhibition in vivo is described below: androstenedione (30 mg/kg subcutaneously) is administered on its own or together with a compound of the invention (orally or subcutaneously) over a period of 4 days to sexually immature female rats. After the fourth administration the rats are sacrificed, and the uteri are isolated and weighed. The inhibition of aromatase is determined by the extent to which hypertrophy of the uterus caused by the administration of androstenedione alone is prevented or reduced by the simultaneous administration of the compound of the invention. The minimum effective dose of the compounds of the invention in the in vivo tests is approximately from 0.001 to 1 mg/kg.

The anti-tumour activity, especially in the case of oestrogen-dependent tumours, can be demonstrated in vivo, for example in DMBA-induced mammary tumours in female Sprague-Dawley rats [see Proc. Soc. Exp. Biol. Med. 160, 296–301 (1979)]. The administration of compounds of the invention brings about a regression of the tumours and also suppresses the occurrence of new tumours at daily doses of 1 mg/kg p.o. and above.

Furthermore, the compounds of formula I have no inhibitory action on the cleavage of the cholesterol side chain and do not induce adrenal hypertrophy, which is demonstrated by endocrinal organ investigations.

On account of their pharmacological properties as extremely selective inhibitors of the enzyme aromatase, the compounds of formula I are suitable, for example, for the treatment of oestrogen-dependent diseases, such as breast tumours (breast cancer), endometriosis, premature labour or endometrial tumours in women or gynaecomastia in men.

The invention preferably relates to compounds of formula I wherein Tetr is 1- or 2-tetrazolyl that is unsubstituted or substituted in the 5-position by lower alkyl, phenyl-lower alkyl or by lower alkanoyl; $R_1$ and $R_2$ are each independently of the other hydrogen; lower alkyl that is unsubstituted or substituted by hydroxy, lower alkoxy, halogen, carboxy, lower alkoxycarbonyl, (amino, lower alkylamino or di-lower alkylamino)-carbonyl or by cyano; lower alkenyl, aryl, hetaryl, aryl-lower alkyl, $C_3$–$C_6$cycloalkyl, $C_3$–$C_6$cycloalkyllower alkyl, lower alkylthio, arylthio or aryl-lower alkylthio; or $R_1$ and $R_2$ together are $C_4$–$C_6$straight-chain alkylene that is unsubstituted or substituted by lower alkyl, or are a group —$(CH_2)_m$—1,2-phenylene—$(CH_2)_n$—, wherein m and n are each independently of the other 1 or 2 and 1,2-phenylene is unsubstituted or substituted in the same manner as phenyl in accordance with the definition of aryl below, or are lower alkylidene that is unsubstituted or mono- or di-substituted by aryl; and R and $R_0$ are each independently of the other hydrogen or lower alkyl; or R and $R_0$ together, located at adjacent carbon atoms of the benzene ring, form a benzo group that is unsubstituted or substituted in the same manner as phenyl in accordance with the definition of aryl below; and in the above definitions aryl is in each case phenyl that is unsubstituted or substituted by one or more substituents from the group consisting of lower alkyl, lower alkoxy, hydroxy, lower alkanoyloxy, nitro, amino, halogen, trifluoromethyl, carboxy, lower alkoxycarbonyl, (amino, lower alkylamino or di-lower alkylamino)-carbonyl, cyano, lower alkanoyl, benzoyl, lower alkylsulfonyl and (amino, lower alkylamino or di-lower alkylamino)-sulfonyl; and in the above definitions hetaryl is an aromatic heterocyclic radical from the group consisting of pyrrolyl, pyrazolyl, imidazolyl, triazolyl, tetrazolyl, furanyl, thienyl, isoxazolyl, oxazolyl, oxadiazolyl, isothiazolyl, thiazolyl, thiadiazolyl, pyridyl, pyridazinyl, pyrimidinyl, pyrazinyl, triazinyl, indolyl, isoindolyl, benzimidazolyl, benzotriazolyl, benzofuranyl, benzothienyl, benzoxazolyl, benzothiazolyl, benzoxadiazolyl, benzothiadiazolyl, quinolyl and isoquinolyl, which radical is unsubstituted or substituted in the same manner as phenyl in accordance with the definition of aryl above; and salts thereof.

Special preference is given to the compounds of formula I wherein Tetr is 1- or 2-tetrazolyl; $R_1$ and $R_2$ are each independently of the other hydrogen; lower alkyl that is unsubstituted or substituted by hydroxy, lower alkoxy, halogen, carboxy, lower alkoxycarbonyl, (amino, lower alkylamino or di-lower alkylamino)-carbonyl or by cyano; lower alkenyl, aryl, hetaryl, aryl-lower alkyl, $C_3$–$C_6$cycloalkyl, $C_3$–$C_6$cycloalkyl-lower alkyl, lower alkylthio, arylthio or aryl-lower alkylthio; or $R_1$ and $R_2$ together are $C_4$–$C_6$-straight-chain alkylene that is unsubstituted or substituted by lower alkyl, or are a group —$(CH_2)_m$—1,2-phenylene—$(CH_2)_n$—, wherein m and n are each independently of the other 1 or 2 and 1,2-phenylene is unsubstituted or substituted in the same manner as phenyl in accordance with the definition of aryl below, or are lower alkylidene that is unsubstituted or mono- or di-substituted by aryl; and R and $R_0$ are each independently of the other hydrogen or lower alkyl; or R and $R_0$ together, located at adjacent carbon atoms of the benzene ring, form a benzo group that is unsubstituted or substituted in the same manner as phenyl in accordance with the definition of aryl below; and in the above definitions aryl is in each case phenyl that is unsubstituted or substituted by one or two substituents from the group consisting of lower alkyl, lower alkoxy, hydroxy, lower alkanoyloxy, nitro, amino, halogen, trifluoromethyl, carboxy, lower alkoxycarbonyl, (amino, lower alkylamino or di-lower alkylamino)-carbonyl, cyano, lower alkanoyl, benzoyl, lower alkylsulfonyl and (amino, lower alkylamino or di-lower alkylamino)-sulfonyl; and in the above definitions hetaryl is an aromatic heterocyclic radical from the group consisting of thienyl, indolyl, pyridyl, furyl and benzofuranyl, which radical is unsubstituted or substituted by from 1 to 3 substituents from the group consisting of lower alkyl, lower alkoxy, cyano and halogen, or is benzotriazolyl that in the 1-position is unsubstituted or substituted by lower alkyl, hydroxy or by lower alkoxy; and salts thereof.

Preference is given especially to the compounds of formula I wherein Tetr is 1- or 2-tetrazolyl; $R_1$ and $R_2$ are each independently of the other hydrogen; lower alkyl that is unsubstituted or substituted by lower alkoxycarbonyl; phenyl that is unsubstituted or substituted by cyano, halogen, lower alkoxy, lower alkyl or by hydroxy-lower alkyl; thienyl, pyridyl; 1-lower alkyl-1H-benzotriazolyl; phenyl-lower alkyl that in the phenyl ring is unsubstituted or substituted by cyano; lower alkylthio or phenylthio; or $R_1$ and $R_2$ together are $C_4$–$C_5$straight-chain alkylene or a group —$CH_2$—1,2-phenylene—$CH_2$—; and R and $R_0$ are hydrogen; or R and $R_0$ together, located at adjacent carbon atoms of the benzene ring, form a benzo group; and salts thereof.

Very special preference is given to compounds of formula I wherein Tetr is 1- or 2-tetrazolyl, $R_1$ is hydrogen, lower alkyl; phenyl that is unsubstituted or substituted by cyano, halogen, lower alkoxy or by lower alkyl; or phenyl-lower alkyl; and R, $R_0$ and $R_2$ are hydrogen, and salts thereof.

Also preferred are the compounds of formula I wherein Tetr is 1- or 2-tetrazolyl; $R_1$ is hydrogen; lower alkyl that is unsubstituted or substituted by hydroxy, lower alkoxy, halogen, carboxy, lower alkoxycarbonyl, (amino, lower alkylamino or di-lower alkylamino)-carbonyl or by cyano; lower alkenyl, aryl, hetaryl, aryl-lower alkyl, $C_3$–$C_6$-cycloalkyl, $C_3$–$C_6$cycloalkyl-lower alkyl, lower alkylthio, arylthio or aryl-lower alkylthio; $R_2$ is hydrogen; or $R_1$ and $R_2$ together are $C_4$–$C_6$-straight-chain alkylene that is unsubstituted or substituted by lower alkyl, or are a group —$(CH_2)_m$—1,2- phenylene—$(CH_2)_n$—, wherein m and n are each independently of the other 1 or 2 and 1,2-phenylene is unsubstituted or substituted in the same manner as phenyl in accordance with the definition of aryl below, or are lower alkylidene that is unsubstituted or mono- or disubstituted by aryl; and R and $R_0$ are each independently of the other hydrogen or lower alkyl; or R and $R_0$ together, located at adjacent carbon atoms of the benzene ring, form a benzo group that is unsubstituted or substituted in the same manner as phenyl in accordance with the definition of aryl below; and in the above definitions aryl is in each case phenyl that is unsubstituted or substituted by a substituent from the group consisting of lower alkyl, lower alkoxy, hydroxy, lower alkanoyloxy, nitro, amino, halogen, trifluoromethyl, carboxy, lower alkoxycarbonyl, (amino, lower alkylamino or di-lower alkylamino)-carbonyl, cyano, lower alkanoyl, benzoyl, lower alkylsulfonyl and (amino, lower alkylamino or di-lower alkylamino)-sulfonyl; and in the above definitions hetaryl is an aromatic heterocyclic radical from the group consisting of thienyl, indolyl, pyridyl, furyl and benzofuranyl, which radical is unsubstituted or substituted by 1 or 2 substituents from the group consisting of lower alkyl, lower alkoxy, cyano and halogen, or is benzotriazoyl that in the 1-position is unsubstituted or substituted by lower alkyl, hydroxy or by lower alkoxy; and salts thereof.

Special preference is given to the compounds of formula I wherein Tetr is 1- or 2-tetrazolyl; $R_1$ is hydrogen; lower alkyl that is unsubstituted or substituted by lower alkoxycarbonyl; phenyl that is unsubstituted or substituted by cyano, halogen, lower alkoxy, lower alkyl or by hydroxy-lower alkyl; thienyl, pyridyl; phenyl-lower alkyl that in the phenyl ring is unsubstituted or substituted by cyano; lower alkylthio or phenylthio; $R_2$ is hydrogen; or $R_1$ and $R_2$ together are $C_4$-$C_5$straight-chain alkylene or a group —$CH_2$—1,2-phenylene—$CH_2$—; and R and $R_0$ are hydrogen; or R and $R_0$ together, located at adjacent carbon atoms of the benzene ring, form a benzo group; and salts thereof.

Special mention should be made of the following sub-groups of a group of compounds of formula I: (a) compounds of formula I wherein the radical Tetr is 2-tetrazolyl; (b) compounds of formula I wherein the radical Tetr is 1-tetrazolyl; (c) compounds of formula I wherein the radical —$CR_1R_2$(Tetr) is linked in the p-position to the cyano group; (d) compounds of formula I wherein $R_2$ is hydrogen; (e) compounds of formula I wherein $R_1$ is phenyl that is unsubstituted or monosubstituted by cyano, halogen, lower alkoxy or by lower alkyl and $R_2$ is hydrogen; (f) compounds of formula I wherein R and $R_0$ are hydrogen.

The invention relates especially to the specific compounds described in the Examples and pharmaceutically acceptable salts thereof.

The compounds of formula I can be prepared in a manner known per se, for example by (a) reacting a reactive esterified derivative of a compound of formula II,

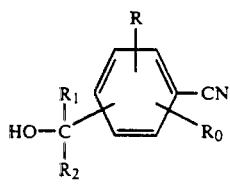

(II)

wherein R, $R_0$, $R_1$ and $R_2$ are as defined under formula I, with a compound of formula III, Tetr-H (III)

wherein Tetr is tetrazolyl, or with an N-protected derivative thereof, or (b) for the preparation of compounds of formula I wherein Tetr is 1-tetrazolyl, in a compound of formula IV,

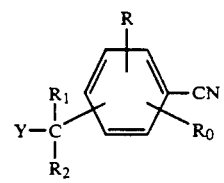

(IV)

wherein Y is a radical that can be converted into 1-tetrazolyl and R, $R_0$, $R_1$ and $R_2$ are as defined under formula I, converting Y into 1-tetrazolyl, or (c) reacting a compound of formula V,

(V)

wherein Tetr, $R_1$ and $R_2$ are as defined under formula I, in a basic medium with a compound of formula VI,

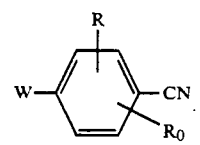

(VI)

wherein W is a leaving group and R and $R_0$ are as defined under formula I, or (d) in a compound of formula VII,

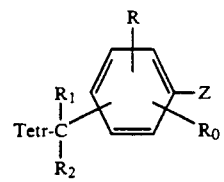

(VII)

wherein Z is a radical that can be converted into cyano and Tetr, R, $R_0$, $R_1$ and $R_2$ are as defined under formula I, converting the radical Z into a cyano group; and/or, if desired, converting a resulting compound of formula I into a different compound of formula I, and/or, if desired, converting a resulting salt into the free compound or into a different salt, and/or, if desired, converting a resulting free compound of formula I into a salt, and/or separating a resulting mixture of isomeric compounds of formula I into the individual isomers.

In the following more detailed description of processes (a), (b), (c) and (d), unless otherwise indicated the symbols Tetr, R, $R_0$, $R_1$ and $R_2$ are each as defined under formula I.

PROCESS (A)

In a compound of formula II, a reactive esterified derivative of the hydroxymethyl group —CR₁R₂OH is (unsubstituted or substituted) hydroxymethyl that has been esterified by a leaving group, for example lower alkyl- or aryl-sulfonyloxymethyl, such as methylsulfonyloxymethyl or p-toluenesulfonyloxymethyl, or halomethyl, for example chloromethyl, bromomethyl or iodomethyl.

If tetrazole is used as the compound of formula III in the reaction according to process (a), then there are usually obtained mixtures of compounds of formula I wherein Tetr is 1-tetrazolyl, 2-tetrazolyl or 5-tetrazolyl, which can readily be separated, for example by chromatography. In some cases, by using compounds of formula III wherein a certain ring nitrogen atom has been protected by a protecting group, it is possible to obtain selectively only one of the compounds in question.

Suitable protecting groups for a ring nitrogen atom in a compound of formula III are, for example, tri-lower alkylsilyl, for example trimethylsilyl, lower alkanoyl, for example acetyl, di-lower alkylaminocarbonyl, for example dimethylaminocarbonyl, or triarylmethyl, for example triphenylmethyl.

The condensation reaction according to process (a) is known per se and corresponds to a customary N-alkylation reaction, which is carried out, for example, without the addition of bases or, preferably, in the presence of bases, for example potassium carbonate, sodium, triethylamine or pyridine.

Reactive esterified derivatives of the compounds of formula II are known per se or are obtained, for example, in a manner known per se from the corresponding hydroxymethyl compounds by esterification. The hydroxymethyl compounds can be obtained, for example by reduction, for example with LiAlH₄ or diisobutylaluminium hydride, from the corresponding carboxy or lower alkoxy-carbonyl compounds. The latter are known per se or can be prepared analogously to known substituted cyanobenzoic acids or their esters.

The reaction according to process (a) is used especially for the preparation of compounds of formula I wherein R₁ and R₂ are hydrogen.

PROCESS (b)

A radical Y that can be converted into 1-tetrazolyl is, for example, isocyano (—N⊕≡C⊖) or amino.

Compounds of formula IV wherein Y is isocyano (isonitriles) are converted into the corresponding 1-tetrazolyl compounds of formula I, for example, by reaction with hydrazoic acid or, especially, with a salt thereof, for example an alkali metal or ammonium azide.

Compounds of formula IV wherein Y is amino are converted into the corresponding 1-tetrazolyl compounds of formula I, for example, by reaction with hydrazoic acid or, especially, with a salt thereof, and with an orthoformic acid tri-lower alkyl ester, for example orthoformic acid triethyl ester.

Isonitriles of formula IV are prepared, for example, from the analogous reactive esterified derivatives of the compounds of formula II wherein the esterified —CR₁R₂OH group is, for example, unsubstituted or α,α'-substituted bromomethyl. The latter are converted into the desired isonitriles of formula IV in a manner known per se, for example either directly with silver cyanide in a polar solvent or, for example, by first reacting them with hexamethylenetetramine (urotropin) to form the corresponding unsubstituted or α,α'-substituted aminomethyl compounds (=compounds of formula IV wherein Y=amino) which are then converted into the desired isonitriles of formula IV in a manner known per se, for example by reaction with dichlorocarbene (for example obtained from chloroform and conc. KOH).

PROCESS (c)

A leaving group W in a compound of formula VI is, for example, halogen, lower alkylsulfonyloxy or arylsulfonyloxy, and preferably fluorine.

Bases suitable for the reaction according to process (c) are, especially, strong bases, for example lithium diisopropylamide, an alkali metal hydride, an alkali metal-lower alkanolate, for example potassium tert.-butanolate, or a strongly basic tertiary amine, for example 1,5-diazabicyclo[4.3.0]non-5-ene (DBN).

The starting compounds of formula V are obtained, for example, by reacting a compound of formula VIII

with tetrazole.

PROCESS (d)

Process (d) is carried out in accordance with known methods for the introduction of the nitrile group.

In a compound of formula VII radicals Z that can be converted into cyano include, for example, hydrogen; esterified hydroxy groups, for example halogen, especially chlorine, bromine or iodine, or a sulfonyloxy group, for example toluenesulfonyloxy, benzenesulfonyloxy or methylsulfonyloxy; sulfo (—SO₃H), amino, carboxy, carboxy in the form of a functional derivative, for example aminocarbonyl, lower alkylaminocarbonyl, for example tert.-butylaminocarbonyl, or haloformyl, for example chloro- or bromo-formyl (—COCl, —COBr), formyl in the form of a functional derivative, for example hydroxyiminomethyl, or halomagnesium, for example iodo-, bromo- or chloro-magnesium.

Compounds of formula I can be obtained according to process (d), for example, by the following reactions:

The reaction of a compound of formula VII wherein Z is hydrogen to form the corresponding nitrile of formula I is effected, for example, in accordance with the known method of C. Friedel, F. M. Crafts and P. Karrer with cyanogen chloride (ClCN) or cyanogen bromide, or in accordance with the method of J. Houben and W. Fischer, for example with trichloroacetonitrile. The customary catalyst, aluminium trichloride, is advantageously used here. In these reactions hydrogen chloride or hydrogen bromide is liberated, which can be removed from the reaction mixture by the addition of a base, preferably an amine, for example triethylamine or pyridine.

The reaction of a compound of formula VII wherein Z is halogen, for example chlorine, bromine or iodine, to form a corresponding nitrile of formula I is carried out, for example, using a cyanide salt, especially sodium or potassium cyanide or, preferably, copper(I) cyanide. Preferred solvents for this reaction are pyridine, quinoline, dimethylformamide, 1-methyl-2-pyrrolidone and hexamethylphosphoric acid triamide. High temperatures, especially the reflux temperature of the reaction mixture, are preferred.

The conversion of a compound of formula VII wherein Z is sulfonyloxy, for example p-toluenesulfonyloxy, benzenesulfonyloxy or methylsulfonyloxy, into a nitrile of formula I is carried out, for example, by reaction with an alkali metal cyanide, preferably sodium or potassium cyanide. High temperatures, especially the reflux temperature of the reaction mixture, are preferred.

The reaction of a compound of formula VII wherein Z is amino to form a nitrile of formula I is effected in several stages. First, for example, a diazonium salt is prepared, for example by reacting the amino compound with an alkali metal nitrite, preferably potassium nitrite. The diazonium salt can then be reacted further in situ using the known Sandmeyer reaction, for example with copper(I) cyanide or a complex cyanide, preferably potassium copper ammonium cyanide, or with a catalytic amount of freshly precipitated copper powder in the presence of an alkali metal cyanide, for example sodium or potassium cyanide.

The reaction of a compound of formula VII wherein Z is carboxy to form a nitrile of formula I can be carried out, for example, by reaction with a chlorosulfonyl isocyanate in, for example, dimethylformamide according to the method of R. Graf in Angew. Chem. 80, 183 (1968).

The reaction of a compound of formula VII wherein Z is carboxy in the form of a functional derivative, for example in the form of aminocarbonyl or lower alkylaminocarbonyl, advantageously tert.-butylaminocarbonyl, to form a nitrile of formula I can be carried out, for example, with a strong dehydrating agent, for example phosphorus(V) oxide, phosphoryl chloride, thionyl chloride, phosgene or oxalyl chloride. The dehydration can preferably be carried out in the presence of a base. A suitable base is, for example, an amine, for example a tertiary amine, for example a tri-lower alkylamine, such as trimethylamine, triethylamine or ethyldiisopropylamine, or an arylalkylamine, for example N,N-dimethylaniline, or a cyclic tertiary amine, for example a lower alkylmorpholine, for example N-methylmorpholine, or, for example, a base of the pyridine type, for example pyridine or quinoline.

The reaction of a compound of formula VII wherein Z is formyl to form a nitrile of formula I is carried out, for example, by converting the formyl group into a reactive, functional derivative, for example hydroxyiminomethyl, and converting that group into a cyano group using a dehydrating agent. A suitable dehydrating agent is one of the inorganic dehydrating agents mentioned above, for example phosphorus(V) chloride, or preferably an anhydride of an organic acid, for example the anhydride of a lower alkanoic acid, for example acetic anhydride. The conversion of the formyl group into the hydroxyiminomethyl group is effected, for example, by reaction with a salt of hydroxylamine, preferably the hydrochloride.

A compound of formula VII wherein Z is formyl can also be converted directly into the corresponding nitrile of formula I, for example by reaction with O,N-bis-(trifluoroacetyl)-hydroxylamine in the presence of a base, for example pyridine, in accordance with the method of D. T. Mowry, Chem. Reves. 42, 251 (1948).

The reaction of a compound of formula VII wherein Z is halomagnesium, for example iodo-, bromo- or chloro-magnesium, to form a corresponding nitrile of formula I is carried out, for example, by reacting a magnesium halide with a cyanogen halide or dicyanogen. The "Grignard" reagent, that is to say a compound of formula VII wherein Z is a halomagnesium group, is prepared by customary processes, for example by reaction of a compound of formula VII wherein Z is halogen, for example chlorine, bromine or iodine, with magnesium, for example in dry ether.

Compounds of formula VII wherein Tetr is 1- or 2-tetrazolyl, $R_1$ is a benzotriazolyl radical of formula (1),

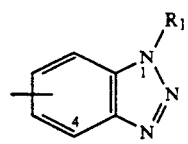

wherein $R_3$ is as defined above under formula (1), R, $R_0$ and $R_2$ are hydrogen, or R and $R_0$ together, located at adjacent carbon atoms of the benzene ring, form a benzo group, and Z is chlorine or bromine, and salts thereof, are valuable intermediates for the preparation of the corresponding cyano compounds of formula I. Furthermore, like the compounds of formula I, they are effective as inhibitors of aromatase and the invention relates to these compounds also.

Compounds of formula I can be converted into different compounds of formula I.

For example, compounds of formula I wherein $R_1$ and $R_2$ are hydrogen can be converted by reaction with a reactive functional derivative of $R_1$ or $R_2$ ($R_1 \neq H$, $R_2 \neq H$) into compounds of formula I wherein one of the radicals $R_1$ and $R_2$ is hydrogen and the other of the radicals $R_1$ and $R_2$ is other than hydrogen.

Compounds of formula I wherein one of the radicals $R_1$ and $R_2$ is hydrogen and the other of the radicals $R_1$ and $R_2$ is other than hydrogen can in turn be converted by reaction with a reactive functional derivative of $R_1$ or $R_2$ ($R_1 \neq H$, $R_2 \neq H$) into compounds of formula I wherein $R_1$ and $R_2$ are other than hydrogen.

Furthermore, compounds of formula I wherein $R_1$ and $R_2$ are hydrogen can be converted by reaction with a reactive functional derivative of $R_1$ or $R_2$ ($R_1 \neq H$, $R_2 \neq H$), or with a bifunctional derivative of a radical formed by $R_1$ and $R_2$ together, into compounds of formula I wherein $R_1$ and $R_2$ are other than hydrogen and wherein either $R_1$ is identical to $R_2$ or $R_1$ and $R_2$ together form a radical as defined under formula I.

Functional derivatives of $R_1$ and/or $R_2$ are, for example, halogen derivatives, for example chlorine or bromine derivatives, or sulfonyloxy derivatives, for example lower alkylsulfonyloxy or arylsulfonyloxy.

The corresponding condensation reactions are carried out in a manner known per se, for example by first of all preparing a carbanion of the compound of formula I wherein $R_1 = R_2 = H$ or $R_1 = H$, $R_2 \neq H$ or $R_1 \neq H$, $R_2 = H$, in the presence of a strong base, for example lithium diisopropylamide, an alkali metal hydride, an alkali metal lower alkanolate, such as potassium tert.-butanolate, or a strongly basic tertiary amine, such as 1,5-diazabicyclo[4.3.0]non-5-ene (DBN), preferably under a protective gas atmosphere, for example under a nitrogen atmosphere, and in an inert solvent, for example dimethylformamide, and then reacting the carbanion so prepared with a functional derivative of $R_1$ or $R_2$, or $R_1 + R_2$.

For compounds of formula I in which $R_1$ and/or $R_2$ are 4-cyanophenyl, a suitable reactive derivative is p-fluorobenzonitrile. The reaction is then carried out in the same manner as that described for process (c). For compounds in which $R_1$ or $R_2$ is (lower alkyl, aryl or aryl-lower alkyl)thio, suitable reactive derivatives are the corresponding disulfides, for example dimethyl disulfide, diphenyl disulfide or dibenzyl disulfide.

Furthermore, compounds of formula I wherein Tetr is 1- or 2-tetrazolyl can be converted in a manner known per se into compounds of formula I wherein Tetr is 1- or 2-tetrazolyl that is substituted in the 5-position. For example, alkylation, for example with lower alkyl halides or aryl-lower alkyl halides, can be used to introduce lower alkyl or aryl-lower alkyl groups, respectively. Furthermore, for example, acylation, for example with lower alkanoic acid halides or anhydrides, can be used to introduce lower alkanoyl groups.

Free compounds of formula I having salt-forming properties obtainable in accordance with the process can be converted into their salts in a manner known per se; for example, compounds having basic properties can be converted by treatment with acids or suitable derivatives thereof, while compounds having acidic properties can be converted, for example, by treatment with bases or suitable derivatives thereof.

Mixtures of isomers obtainable in accordance with the invention can be separated into the individual isomers in a manner known per se; for example, racemates can be separated by formation of salts with optically pure salt-forming reagents and separation of the resulting diastereoisomeric mixture, for example by means of fractional crystallisation.

The above-mentioned reactions can be carried out under reaction conditions known per se, in the absence or, usually, in the presence of solvents or diluents, preferably those solvents or diluents that are inert towards the reagents used and are solvents therefor, in the absence or presence of catalysts, condensation agents or neutralising agents, and, depending upon the nature of the reaction and/or the reactants, at reduced, normal or elevated temperature, for example in a temperature range of from approximately $-70°$ C. to approximately $200°$ C., preferably from approximately $-20°$ C. to approximately $150°$ C., for example at the boiling point of the solvent used, under atmospheric pressure or in a closed vessel, optionally under pressure, and/or in an inert atmosphere, for example under a nitrogen atmosphere.

In view of the close relationship between the compounds of formula I in free form and in the form of salts, hereinbefore and hereinafter any reference to the free compounds or their salts should be understood as including also the corresponding salts or free compounds, respectively, where appropriate and expedient.

The compounds, including their salts, may also be obtained in the form of hydrates, or their crystals may, for example, include the solvent used for crystallisation.

In the process of this invention it is preferable to use those starting materials which result in the compounds described at the beginning as being especially valuable.

The invention relates also to those forms of the process in which a compound obtainable as intermediate at any stage of the process is used as starting material and the remaining process steps are carried out, or in which a starting material is formed under the reaction conditions or is used in the form of a derivative, for example a salt thereof.

The present invention relates also to pharmaceutical preparations that contain one of the pharmacologically active compounds of formula I as active ingredient. Preparations for enteral, especially oral, and for parenteral administration are especially preferred. The preparations contain the active ingredient on its own or, preferably, together with a pharmaceutically acceptable carrier. The dosage of the active ingredient depends upon the disease to be treated and upon the species, its age, weight and individual condition, and also upon the mode of administration.

The pharmaceutical preparations contain from approximately 0.1% to approximately 95% active ingredient, forms of administration in single dose form preferably containing from approximately 1% to approximately 90% active ingredient and forms of administration that are not in single dose form preferably containing from approximately 0.1% to approximately 20% active ingredient. Dosage unit forms, such as dragées, tablets or capsules, contain from approximately 0.5 mg to approximately 100 mg of active ingredient.

The pharmaceutical preparations of this invention are prepared in a manner known per se, for example by means of conventional mixing, granulating, confectioning, dissolving or lyophilising processes. For example, pharmaceutical preparations for oral use can be obtained by combining the active ingredient with one or more solid carriers, optionally granulating a resulting mixture, and, if desired, processing the mixture or granulate, if necessary with the addition of additional adjuncts, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, alginic acid or a salt thereof, such as sodium alginate. Additional adjuncts are especially flow-regulating agents and lubricants, for example silicic acid, talc, stearic acid or salts thereof, such as magnesium or calcium stearate, and/or polyethylene glycol, or derivatives thereof.

Dragée cores can be provided with suitable coatings which may be resistant to gastric juices, there being used inter alia concentrated sugar solutions which may contain gum arabic, talc, polyvinylpyrrolidone, polyethylene glycol and/or titanium dioxide, or lacquer solutions in suitable organic solvents or solvent mixtures, or, for the production of coatings that are resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Orally administrable pharmaceutical preparations also include dry-filled capsules consisting of gelatin, and also soft, sealed capsules consisting of gelatin and a plasticiser, such as glycerol or sorbitol. The dry-filled capsules may contain the active ingredient in the form of a granulate, for example in admixture with fillers, such as corn starch, binders and/or glidants, such as talc or magnesium stearate, and optionally stabilisers. In soft capsules, the active ingredient is preferably dissolved or suspended in suitable liquid adjuncts, such as fatty oils, paraffin oil or liquid polyethylene glycols, to which stabilisers may also be added.

Other oral forms of administration are, for example, syrups prepared in customary manner which contain the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single dose quantities.

Suitable rectally administrable pharmaceutical preparations are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration there are suitable, especially, aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilisers. The active ingredient, optionally together with adjuncts, can also be in the form of a lyophilisate and can be made into a solution prior to parenteral administration by the addition of suitable solvents. Solutions used, for example, for parenteral administration can also be used as infusion solutions.

The invention relates also to a method of treating the above-mentioned pathological conditions. The compounds of this invention can be administered prophylactically or therapeutically, preferably in the form of pharmaceutical preparations. In the case of an individual having a body weight of about 70 kg the daily dose administered is from approximately 0.5 mg to approximately 100 mg, preferably from approximately 1 mg to approximately 20 mg, of a compound of the present invention.

The following Examples illustrate the present invention; temperatures are given in degrees Celsius. The following abbreviations are used: ether=diethyl ether; THF=tetrahydrofuran; hexane=n-hexane; DMSO=-dimethyl sulfoxide; DMF=dimethylformamide; TLC=thin-layer chromatography.

Example 1: 4-(2-Tetrazolyl)methyl-benzonitrile and 4-(1-tetrazolyl)methyl-benzonitrile 6.3 g of tetrazole, 8.28 g of potassium carbonate and 0.675 g of potassium iodide are added in succession to a solution of 12 g of 4-bromomethylbenzonitrile in 400 ml of acetone and the mixture is then stirred for 19 hours at 40°–45°. The reaction mixture is cooled, filtered and concentrated. The residue is partitioned between $CH_2Cl_2$ and water. The organic phase is washed with brine, dried over sodium sulfate and then concentrated by evaporation. Subsequent chromatography (silica gel) yields first, with toluene/ethyl acetate (2:1), 4-(2-tet-razolyl)methyl-benzonitrile [TLC (hexane/ethyl acetate, 1:2) $R_f$=0.76); $^1$H-NMR (CDCl$_3$): $\delta$=5.8 (2H, s), 7.4 and 7.7 (4H, m), 8.5 (1H, s) ppm], and then, with ethyl acetate, 4-(1-tetrazolyl)methyl-benzonitrile [TLC (hexane/ethyl acetate, 1:2), $R_f$=0.36); $^1$H-NMR (CDCl$_3$): $\delta$=5.63 (2H, s), 7.4 and 7.7 (4H, m), 8.6 (1H, s) ppm].

Example 2: 4-[α-(4-Cyanophenyl)-(2-tetrazolyl)methyl]-benzonitrile

A solution of 4.6 g of 4-[(2-tetrazolyl)methyl]-benzonitrile (see Example 1) in 37 ml of absolute DMF is added at room temperature within a period of 30 minutes to a solution of 7.9 g of potassium tert.-butanolate in 37 ml of absolute DMF. The dark green solution is stirred for 15 minutes and then a solution of 3.8 of 4-fluorobenzonitrile in 37 ml of absolute DMF is added within a further period of 15 minutes. The dark, reddish-brown reaction mixture is stirred for 1.5 hours to complete the reaction, and then diluted with 30 ml of $CH_2Cl_2$. After cooling to 0°, the mixture is rendered neutral with 6N HCl, and the solvents are then evaporated off under reduced pressure. The resulting resin is partitioned between $CH_2Cl_2$ and water, and the organic solution is separated off and washed again with brine and dried over sodium sulfate. Purification is effected by column chromatography [silica gel, hexane/ethyl acetate (2:1)] and subsequent crystallisation from ether; m.p. 110°–112°; IR($CH_2Cl_2$): 2220, 1605, 1497, 1410 cm$^{-1}$; $^1$H-NMR (DMSO-d$_6$): $\delta$=7.48 and 7.92 (8H, m), 8.08 (1H, s), 9.18 (1H, s) ppm.

Example 3: 1-Cyano-4-(1-tetrazolyl)methyl-naphthalene and 1-cyano-4-(2-tetrazolyl)methyl-naphthalene 420 mg of tetrazole, 553 mg of potassium carbonate and 53 mg of potassium iodide are added to a solution of 985 mg of 1-cyano-4-bromomethyl-naphthalene in 20 ml acetone, and the mixture is stirred for 3.5 hours at 45°. After the reaction mixture has cooled, the solvent is distilled off and the residue is dissolved in methylene chloride. The organic solution is washed with water and brine, then dried over sodium sulfate and concentrated. Separation by column chromatography yields first, by elution with toluene/ethyl acetate (9:1), 1-cyano-4-(2-tetrazolyl)methyl-naphthalene, m.p. 124°, [IR($CH_2Cl_2$): 3052, 2225, 1592, 1516 cm$^{-1}$, $^1$H-NMR (DMSO-d$_6$): $\delta$=6.62 (2H, s), 7.6 and 8.2 (2H, m), 7.83 (2H, m), 8.2 and 8.33 (2H, m), 9.02 (1H, s) ppm] and then, with toluene/ethyl acetate (3:1), 1-cyano-4-(1-tetrazolyl)methylnaphthalene, m.p. 171° [IR($CH_2Cl_2$): 3050, 2227, 1516, 1482 cm$^{-1}$; $^1$H-NMR (DMSO-d$_6$): $\delta$=6.36 (2H, s), 7.5 and 8.2 (2H, m), 7.85 (2H, m), 8.2 and 8.37 (2H, m), 9.6 (1H, s) ppm.

Example 4

In a manner analogous to that described in the preceding Examples it is also possible to prepare the following compounds:

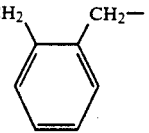

| | Tetr | $R_1$ | $R_2$ | IR(CH$_2$Cl$_2$) [cm$^{-1}$] |
|---|---|---|---|---|
| (a) | 2-tetrazolyl | 2-cyanophenyl | H | 2222, 1593 |
| (b) | 2-tetrazolyl | 4-chlorophenyl | H | 2224, 1596 |
| (c) | 2-tetrazolyl | 4-methoxyphenyl | H | 2222, 1594 |
| (d) | 2-tetrazolyl | 3-pyridyl | H | 2226, 1597 |
| (e) | 2-tetrazolyl | 2-thienyl | H | 2228, 1600 |
| (f) | 2-tetrazolyl | 3-thienyl | H | 2225, 1597 |
| (g) | 2-tetrazolyl | phenyl | H | 2225, 1599 |
| (h) | 2-tetrazolyl | CH$_3$ | H | 2228, 1602 |
| (i) | 2-tetrazolyl | C$_2$H$_5$ | H | 2226, 1600 |
| (j) | 2-tetrazolyl | n-C$_3$H$_7$ | H | 2225, 1601 |
| (k) | 2-tetrazolyl | n-C$_4$H$_9$ | H | 2225, 1601 |
| (l) | 2-tetrazolyl | isopropyl | H | 2226, 1598 |
| (m) | 2-tetrazolyl | n-C$_5$H$_{11}$ | H | 2225, 1599 |
| (n) | 2-tetrazolyl | phenylthio | H | 2228, 1596 |
| (o) | 2-tetrazolyl | 4-methylphenyl | H | 2225, 1598 |
| (p) | 2-tetrazolyl | 4-hydroxymethylphenyl | H | 3520, 2226, 1596 |
| (q) | 2-tetrazolyl | benzyl | H | 2224, 1598 |
| (r) | 2-tetrazolyl | 4-cyanobenzyl | H | 2225, 1600 |
| (s) | 2-tetrazolyl | methylthio | H | 2224, 1602 |
| (t) | 2-tetrazolyl | 2-ethoxycarbonylethyl | H | 2225, 1740, 1602 |
| (u) | 2-tetrazolyl | —CH$_2$—CH$_2$—CH$_2$—CH$_2$— | | 2223, 1597 |
| (v) | 2-tetrazolyl | —CH$_2$—(o-C$_6$H$_4$)—CH$_2$— | | 2224, 1597 |
| (w) | 2-tetrazolyl | 4-cyanophenyl | CH$_3$ | 2226, 1600 |
| (x) | 2-tetrazolyl | phenyl | phenyl | 2228, 1598 |
| (y) | 2-tetrazolyl | 4-cyanophenyl | 2-ethoxycarbonylethyl | 2226, 1738, 1600 |

Example 5:
4-[α-(1-Methyl-1H-benzotriazol-6-yl)-(2-tetrazolyl)methyl]-benzonitrile 1-Chloro-4-[α-(1-methyl-1H-benzotriazol-6-yl)-(2-tetrazolyl)-methyl]-benzene is reacted with copper(I) cyanide, yielding the title compound.

The starting compound is prepared as follows:

(a) 1-Methyl-1H-benzotriazole-6-carboxylic acid methyl ester

Benzotriazole-6-carboxylic acid methyl ester is reacted with methyl iodide, yielding the title compound (in addition to the isomeric 2-methyl-2H and 3-methyl-3H compounds).

The title compound is obtained in pure form by chromatography.

(b) 1-Methyl-1H-benzotriazole-6-carboxylic acid

The methyl ester (a) is hydrolysed with NaOH, yielding the title compound.

Alternatively, the title compound can also be obtained from the dimethyl compound of Example 6a by oxidation with KMnO$_4$.

(c) 6-(4-Chlorobenzoyl)-1-methyl-1H-benzotriazole

The carboxylic acid (b) is converted into the corresponding acid chloride with thionyl chloride and then reacted with chlorobenzene and AlCl$_3$, yielding the title compound.

(d) 6-[1-(4-Chlorophenyl)-1-hydroxymethyl]-1-methyl-1H-benzotriazole

The keto compound (c) is reduced with sodium borohydride, yielding the title compound.

Alternatively, the title compound can be obtained from the bromomethyl compound of Example 6b, by (1) oxidation with dimethyl sulfoxide to form 6-formyl-1-methyl-1H-benzotriazole and (2) reaction of the latter compound with 1-chloro-4-chloromagnesium-benzene (Grignard compound).

(e) 6-[1-(4-Chlorophenyl)-1-chloromethyl]-1-methyl-1H-benzotriazole

The alcohol (d) is reacted with phosphorus trichloride, yielding the title compound.

(f) 1-Chloro-4-[α-(1-methyl-1H-benzotriazol-6-yl)-(2-tetrazolyl)methyl]-benzene

The chloromethyl compound (e) is reacted with tetrazole, yielding the title compound.

Example 6:
4-[α-(1-Methyl-1H-benzotriazol-6-yl)-(2-tetrazolyl)methyl]-benzonitrile 1-Methyl-6-(2-tetrazolyl)methyl-1H-benzotriazole is reacted with potassium tert.-butanolate in absolute DMF and with 4-fluorobenzonitrile, yielding the title compound.

The starting compound is prepared as follows:

(a) 1,6-Dimethyl-1H-benzotriazole

6-Methylbenzotriazole is reacted with methyl iodide, yielding the title compound (in addition to the isomeric 2-methyl-2H and 3-methyl-3H compounds). The title compound is obtained in pure form by chromatography.

(b) 6-Bromomethyl-1-methyl-1H-benzotriazole

The dimethyl compound (a) is reacted with N-bromosuccinimide, yielding the title compound.

(c) 1-Methyl-6-(2-tetrazolyl)methyl-1H-benzotriazole

The bromomethyl compound (b) is reacted with tetrazole, yielding the title compound.

Example 7: (a) 4-[α-(4-Cyanophenyl)-(1-tetrazolyl)methyl]-benzonitrile and (b) 4-[α-(4-cyanophenyl)-(2-tetrazolyl)-methyl]-benzonitrile 0.07 ml of triethylamine is added to a solution of 197 mg of 4-[α-(4-cyanophenyl)-methylsulfonyloxymethyl]-benzonitrile in 1 ml of DMF. 35 mg of tetrazole are added to the resulting orange suspension which is then stirred at room temperature for 2 hours. A further 0.07 ml of triethylamine is added and the mixture is stirred for a further 5.75 hours at room temperature and then for 23 hours at 50°. The reaction mixture is diluted with ethyl acetate, washed four times with brine, dried over sodium sulfate and concentrated. Column chromatography (SiO$_2$, 230–400 mesh, toluene to toluene/ethyl acetate 7:3) yields first 4-[α-(4-cyanophenyl)-(2-tetrazolyl)-methyl]-benzonitrile, m.p. 110°–112° (as Example 2), and then 4-[α-(4-cyanophenyl)-(1-tetrazolyl)methyl]-benzonitrile, TLC (toluene/ethyl acetate 1:1) R$_f$=0.28, IR (CH$_2$Cl$_2$): 2220, 1605, 1497, 1460, 1405 cm$^{-1}$; $^1$H-NMR (CDCl$_3$): δ=7.47 and 7.94 (8H, m), 7.7 (1H, s), 9.6 (1H, s) ppm.

The starting material is prepared as follows:

4,4'-Dicyanobenzophenone 8.13 g of CuCN are added to a solution of 5.1 g of 4,4'-dibromobenzophenone in 90 ml of DMF and the mixture is stirred under reflux for 13 hours. After cooling, the reaction mixture is diluted with ethyl acetate, washed twice with 50% aqueous ethylenediamine solution, twice with water and then three times with brine, dried and concentrated. Column chromatography (SiO$_2$, toluene to toluene/ethyl acetate 95:5) yields the crystalline title compound; TLC (toluene/ethyl acetate 9:1): R$_f$=0.34; IR (CH$_2$Cl$_2$): 2220, 1670, 1605, 1405 cm$^{-1}$.

4-[α-(4-Cyanophenyl)-hydroxymethyl]-benzonitrile

While cooling with ice, 125 mg of NaBH$_4$ are added to a suspension of 820 mg of 4,4'-dicyanobenzophenone in 35 ml of methanol and the mixture is stirred for 40 minutes. The reaction mixture is then neutralised with acetic acid and concentrated in vacuo. The residue is partitioned between CH$_2$Cl$_2$ and water, and the organic phase is separated off, washed with brine, dried over sodium sulfate and concentrated. The crystalline residue is recrystallised from ethyl acetate/petroleum ether; m.p. 158°; IR (CH$_2$Cl$_2$): 3580, 2220, 1605, 1495 cm$^{-1}$.

4-[α-(4-Cyanophenyl)-methylsulfonyloxymethyl]-benzonitrile

A suspension of 117 mg of 4-[α-(4-cyanophenyl)-hydroxymethyl]-benzonitrile in 1 ml of CH$_2$Cl$_2$ is cooled to 0° and then 0.078 ml of mesyl chloride (=methanesulfonyl chloride) and 0.070 ml of triethylamine are added in succession thereto. After a further 5 hours at 0°, the cooling bath is removed and the mixture is stirred for 2 hours at room temperature to complete the reaction. The reaction mixture is taken up in ethyl acetate, washed with cold aqueous sodium acetate solution and brine, dried over sodium sulfate and concentrated. The crude substance is used without further purification; IR (CH$_2$Cl$_2$): 2220, 1605, 1365, 1170 cm$^{-1}$.

Example 8

10,000 tablets are prepared, each tablet containing 5 mg of active ingredient, for example one of the compounds prepared in Examples 1–7:

| Composition: | |
| --- | --- |
| active ingredient | 50.00 g |
| lactose | 2535.00 g |
| corn starch | 125.00 g |
| polyethylene glycol 6000 | 150.00 g |
| magnesium stearate | 40.00 g |
| purified water | quantum statis |

Process

All the pulverulent constituents are passed through a sieve of 0.6 mm mesh size. Then the active ingredient, the lactose, the magnesium stearate and half the starch are mixed together in a suitable mixer. The other half of the starch is suspended in 65 ml of water and the resulting suspension is added to a boiling solution of the polyethylene glycol in 260 ml of water. The resulting paste is added to the pulverulent mixture and then granulated, if necessary with the addition of more water. The granulate is dried overnight at 35° C., forced through a sieve of 1.2 mm mesh size and compressed to form tablets having a breaking groove.

Example 9

1000 capsules are prepared, each capsule containing 10 mg of active ingredient, for example one of the compounds prepared in Examples 1–7:

| Composition: | |
| --- | --- |
| active ingredient | 10.00 g |
| lactose | 207.00 g |
| modified starch | 80.00 g |
| magnesium stearate | 3.00 g |

Process

All the pulverulent constituents are passed through a sieve of 0.6 mm mesh size. Then, in a suitable mixer, the active ingredient is mixed first with the magnesium stearate and then with the lactose and starch until homogeneous. Hard gelatine capsules No. 2 are each filled with 300 mg of the resulting mixture using a capsule-filling machine.

What is claimed is:

1. A compound of formula I

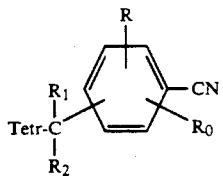

(I)

wherein
Tetr is 1- or 2-tetrazolyl that is unsubstituted or substituted in the 5-position by a first-substituent selected from lower alkyl, phenyl-lower alkyl, and lower alkanoyl;

$R_1$ and $R_2$ are each independently of the other
  (a) hydrogen;
  (b) lower alkyl that is unsubstituted or substituted by a second-substituent selected from hydroxy, lower alkoxy, halogen, carboxy, lower alkoxycarbonyl, aminocarbonyl, lower alkylaminocarbonyl, di(lower alkyl)aminocarbonyl, or cyano; or
  (c) lower alkenyl, aryl, aryl-lower alkyl, $C_{3-6}$cycloalkyl, $C_{3-6}$cycloalkyl-lower alkyl, lower alkylthio, arylthio, or aryl-lower alkylthio;

or $R_1$ and $R_2$ together are
  (a) $C_{4-6}$ straight-chain alkylene that is unsubstituted or substituted by lower alkyl or
  (b) —$(CH_2)_m$-1,2-phenylene-$(CH_2)_n$-, wherein m and n are each independently of the other 1 or 2 and the phenylene ring thereof is unsubstituted or substituted by one or two third-substituents selected from lower alkyl, lower alkoxy, hydroxy, lower alkanoyloxy, nitro, amino, halogen, trifluoromethyl, carboxy, lower alkoxycarbonyl, aminocarbonyl, lower alkylaminocarbonyl, di(lower alkyl)aminocarbonyl, cyano, lower alkanoyl, benzoyl, lower alkylsulfonyl, aminosulfonyl, lower alkylaminosulfonyl, and di(lower alkyl)aminosulfonyl or
  (c) lower alkylidene that is unsubstituted or mono- or di-substituted by aryl; and R and $R_0$ are each independently of the other hydrogen or lower alkyl; or R and $R_0$ together, located at adjacent carbon atoms of the benzene ring, form a benzo group that is unsubstituted or substituted by one or two substituents selected from said third-substituent;

and "aryl", in each case herein, is phenyl which is unsubstituted or substituted by one or two substituents selected from said third-substituent; and wherein "lower" means up to 7 carbon atoms;

or a salt thereof.

2. A compound of formula I according to claim 1 wherein Tetr is 1-or 2-tetrazolyl;

$R_1$ and $R_2$ are each independently of the other
  (a) hydrogen;
  (b) lower alkyl that is unsubstituted or substituted by a second-substituent selected from hydroxy, lower alkoxy, halogen, carboxy, lower alkoxycarbonyl, aminocarbonyl, lower alkylaminocarbonyl, di(lower alkyl)aminocarbonyl, or cyano; or
  (c) lower alkenyl, aryl, aryl-lower alkyl, $C_{3-6}$cycloalkyl, $C_{3-6}$cycloalkyl-lower alkyl, lower alkylthio, arylthio, or aryl-lower alkylthio;

or $R_1$ and $R_2$ together are
  (a) $C_{4-6}$ straight-chain alkylene that is unsubstituted or substituted by lower alkyl or
  (b) —$(CH_2)_m$-1,2-phenylene-$(CH_2)_n$-, wherein m and n are each independently of the other 1 or 2 and the phenylene ring thereof is unsubstituted or substituted by one or two third-substituents selected from lower alkyl, lower alkoxy, hydroxy, lower alkanoyloxy, nitro, amino, halogen, trifluoromethyl, carboxy, lower alkoxycarbonyl, aminocarbonyl, lower alkylaminocarbonyl, di(lower alkyl)aminocarbonyl, cyano, lower alkanoyl, benzoyl, lower alkylsulfonyl, aminosulfonyl, lower alkylaminosulfonyl, and di(lower alkyl)aminosulfonyl; and R and $R_0$ are each independently of the other hydrogen or lower alkyl; or R and $R_0$ together, located at adjacent carbon atoms of the benzene ring, form a benzo group that is unsubstituted or substituted by one or two substituents selected from said third-substituent;

and "aryl", in each case herein, is phenyl which is unsubstituted or substituted by one or two substituents selected from said third-substituent;

or a salt thereof.

3. A compound of formula I according to claim 2 wherein
Tetr is 1-or 2-tetrazolyl;
$R_1$ is (a) hydrogen;
  (b) lower alkyl that is unsubstituted or substituted by hydroxy, lower alkoxy, halogen, carboxy, lower alkoxycarbonyl, aminocarbonyl, lower alkylaminocarbonyl, di-(lower alkyl)aminocarbonyl, or cyano;
  (c) lower alkenyl, aryl, aryl-lower alkyl, $C_{3-6}$cycloalkyl-lower alkyl, lower alkylthio, arylthio, or aryl-lower alkylthio;

$R_2$ is hydrogen; or $R_1$ and $R_2$ together are (a)$C_{4-6}$straight-chain alkylene that is unsubstituted or substituted by lower alkyl, or a group —$(CH_2)_m$-1,2-phenylene-$(CH_2)_n$- wherein m and n are each independently of the other 1 or 2 and the 1,2-phenylene portion is unsubstituted or substituted with substituents selected from said third-substituent;
  (b) lower alkylidene that is unsubstituted or mono- or di- substituted by aryl;

R and $R_0$ are each independently of the other hydrogen or lower alkyl; or

R and $R_0$ together, located at adjacent carbon atoms of the benzene ring, form a benzo group that is unsubstituted or substitued by said third-substituent;

wherein "aryl" is phenyl which is unsubstituted or substituted by said third-substituent; or a salt thereof.

4. A compound of formula I

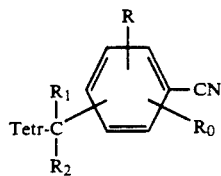

(I)

wherein Tetr is 1-or 2-tetrazolyl;
$R_1$ and $R_2$ are each independently of the other
  (a) hydrogen;

(b) lower alkyl that is unsubstituted or substituted by lower alkoxycarbonyl; or
(c) phenyl that is unsubstituted or substituted by cyano, halogen, lower alkoxy, lower alkyl, or hydroxy-lower alkyl;
(d) phenyl-lower alkyl that is, in the phenyl ring, unsubstituted or substituted by cyano; (e) lower alkylthio or phenylthio;
or $R_1$ and $R_2$ together are
(a) $C_{4-5}$ straight-chain alkylene or
(b) $-CH_2-1,2$-phenylene-$CH_2-$; and
R and $R_0$ are each hydrogen; or
R and $R_0$ together, located at adjacent carbon atoms of the benzene ring, form a benzo group;
or a salt thereof.

5. A compound of formula I according to claim 1 wherein Tetr is 1-or 2-tetrazolyl;
$R_1$ is (a) hydrogen;
(b) lower alkyl;
(c) phenyl that is unsubstituted or substituted by cyano, halogen, lower alkoxy, or lower alkyl; or
(d) phenyl-lower alkyl; and
R, $R_0$, and $R_2$ are hydrogen;
or a pharmaceutically acceptable salt thereof.

6. A compound of formula I according to claim 4, wherein Tetr is 1- or 2- tetrazolyl;
$R_1$ is (a) hydrogen,
(b) lower alkyl that is unsubstituted or substitutedly lower alkoxycarbonyl;
(c) phenyl that is unsubstituted or substituted by cyano, halogen, lower alkoxy, lower alkyl, or hydroxy-lower alkyl;
(d) phenyl-lower alkyl that, in the phenyl ring, is substituted or substituted by cyano;
(e) lower alkylthio or phenylthio;
$R_2$ is hydrogen;
or $R_1$ and $R_2$ together are a $C_{4-5}$ straight-chain alkylene or a group $-CH_2-1,2$-phenylene-$CH_2-$;
R and $R_0$ are hydrogen; or
R and $R_0$ together, located at adjacent carbon atoms of the benzene ring, form a benzo group; or a pharmaceutically acceptable salt thereof.

7. 4-(2-Tetrazolyl)methyl-benzonitrile according to claim 1, or a pharmaceutically acceptable salt thereof.

8. 4-(1-Tetrazolyl)methyl-benzonitrile according to claim 2, or a pharmaceutically acceptable salt thereof.

9. 4-[α-(4-Cyanophenyl)-(2-tetrazolyl)methyl]-benzonitrile according to claim 1, or a pharmaceutically acceptable salt thereof.

10. 4-[α-(4-Cyanophenyl)-(1-tetrazolyl)methyl]-benzonitrile according to claim 1, or a pharmaceutically acceptable salt thereof.

11. A pharmaceutical composition for the treatment of diseases responsive to aromatase inhibition comprising an effective amount of a compound of claim 1 pharmaceutically acceptable salt thereof in combination with one or more phamaceutically acceptable carriers therefor 12. The composition of claim 11 wherein said compound is 4-[alpha-(4-cyanophenyl)-(2-tetrazolyl)methyl]-benzonitrile or a pharmaceutically acceptable salt thereof.

13. A method of inhibiting aromatase activity in mammals which comprises administering to a mammal in need thereof an effective amount of a compound of formula I according to claim 1.

14. A method according to claim 1 wherein the compound being administered is 4-[alpha-(4-cyanophenyl)-(2-tetrazolyl)methyl]-benzonitrile or 2 pharmaceutically acceptable salt thereof.

* * * * *

UNITED STATES PATENT AND TRADEMARK OFFICE
CERTIFICATE OF CORRECTION

PATENT NO. : 5,073,574
DATED : December 17, 1991
INVENTOR(S) : MARC LANG

It is certified that error appears in the above-identified patent and that said Letters Patent is hereby corrected as shown below:

In claim 3, column 22, line 35, after "aryl-lower alkyl," insert --$C_3$-$C_6$ cycloalkyl,--

In claim 6, column 23, line 29, after "unsubstituted or " delete "substitutedly" and insert therefor --substituted by--.

In claim 6, line 35, delete "substituted or substituted" and insert therefor-- unsubstituted or substituted--.

In claim 8, column 24, line 11, after "claim" delete "2" and insert --1--therefor.

In claim 11, column 24, line 20, after "claim 1" insert --or a--.

In claim 14, column 24, line 32, after "claim" delete "1" and insert therefor--13-- and in line 34 after "or" delete "2" and insert therefor --a--

Signed and Sealed this

Seventh Day of December, 1993

Attest:

BRUCE LEHMAN

Attesting Officer

Commissioner of Patents and Trademarks